United States Patent [19]

Markland, Jr. et al.

[11] Patent Number: 4,610,879

[45] Date of Patent: Sep. 9, 1986

[54] FIBRINOLYTIC ENZYME FROM SNAKE VERNOM

[75] Inventors: Francis S. Markland, Jr., Northridge; Nagendranath K. Reddy, Hacienda Heights, both of Calif.

[73] Assignee: University of Southern California, Los Angeles, Calif.

[21] Appl. No.: 568,864

[22] Filed: Jan. 6, 1984

[51] Int. Cl.[4] .................. A61K 37/54; A61K 35/58; C12N 9/48; C12N 9/68; C12N 9/64

[52] U.S. Cl. ........................................ 424/94; 424/98; 435/212; 435/217; 435/226

[58] Field of Search .............. 435/212, 226, 217; 424/94, 98

[56] References Cited

U.S. PATENT DOCUMENTS

| | | | |
|---|---|---|---|
| 3,879,369 | 4/1975 | Nolan | 424/98 X |
| 4,012,502 | 3/1977 | Philpot, Jr. | 424/98 |
| 4,027,012 | 5/1977 | Antonini | 424/98 |
| 4,350,625 | 9/1982 | Abe | 435/98 X |
| 4,461,833 | 7/1984 | Gordon | 435/217 X |

OTHER PUBLICATIONS

Methods in Enzymology vol. 80, pp. 275–285, (1981).

*Primary Examiner*—Lionel M. Shapiro
*Attorney, Agent, or Firm*—Nilsson, Robbins, Dalgarn, Berliner, Carson & Wurst

[57] ABSTRACT

A protease moiety having direct fibrinolytic activity which is useful in thrombolytic therapy is isolated from snake venom and shown to comprise a metalloproteinase having a molecular weight of from 25 to 27 kd and an isoelectric point of about 6.5 to 7.0. The moiety is separated from venom by a series of diverse fractionation steps including molecular sieve, ion-exchange and affinity chromatography.

3 Claims, 7 Drawing Figures

FIBRINOLYTIC ENZYME FROM SNAKE VERNOM

The Government may have rights in this invention pursuant to NIH Grant No. 5K04 HL00869-05.

FIELD OF THE INVENTION

This invention relates generally to the field of chemistry and, more particularly, to the field of biochemistry and the treatment of thromboembolic disease.

BACKGROUND AND SUMMARY OF THE INVENTION

Thromboembolic vascular disease comprises a significant fraction of all morbidity and mortality in the United States. Thrombolytic therapy, using systemically or selectively administered plasminogen activators, has gained increasing acceptance for the treatment of thromboembolic disease. However, further improvements in thrombolytic therapy are still required.

Various compounds have been employed for the intravascular dissolution of thrombi and emboli in mammals. For example, heparin, coumarins, trypsin, chymotrypsin, streptokinase, urokinase, staphylokinase, plasmin and certain snake venoms have been studied and shown to be fibrinolytic in vitro. However, these fibrinolytic agents each produce certain undesirable side effects. For example, anti-coagulants such as heparin, while useful in many instances, must be used with extreme caution in disease states where there is increased danger of hemorrhage.

Urokinase and streptokinase operate by the conversion of plasminogen to the proteolytic enzyme plasmin, which degrades fibrin clots as well as other plasma proteins. When plasmin formed by these plasminogen activators exceeds the capacity of the circulating plasmin inhibitor, $\alpha 2$-antiplasmin, fibrinogen and several other clotting factors will be depleted, enhancing the probability of hemorrhagic complications, common after thrombolytic therapy. Plasminogen activators also consume plasminogen and may deplete this protein to a level at which further thrombolysis is prohibited. Thus, it has been a desideratum to provide a fibrinolytic agent which acts directly on the appropriate thrombus or embolus, without causing a systemic lysis of fibrin deposits and other plasma proteins.

It is known that various snake venoms actively lyse human blood clots and may have certain advantages over more common fibrinolytic agents. However, such venoms have been shown to include fibrinogenolytic, thrombic, thromboplastic, hemolytic or hemorrhagic properties which contra-indicate their clinical use. While fractionation of the whole venoms has been attempted, the isolation of a pure fibrinolytic fraction having clinical usefulness and which is devoid of toxic activities has not been attained.

According to the present invention, a metalloproteinase moiety having direct fibrinolytic action is provided and isolated from snake venom. The moiety has a molecular weight of from about 25 to 27 kilodaltons (kd) and an isoelectric point of from about 6.5 to 7.0, is free of the toxic side effects hereinbefore described and has a direct fibrinolytic activity that is not readily inhibited by serum antiprotease when employed in vivo. The pure venom fraction may be isolated by the novel combinations of diverse fractionations hereinafter described, or the moiety or active portions thereof may be produced by biochemical methods such as genetic engineering or the like. Thrombolytic therapy is now established as a procedure for the treatment of acute deep-vein thrombosis and pulmonary embolism, and the purified enzyme of the present invention presents a substantial therapeutic advantage as it is able to rapidly lyse thrombi with minimal systemic toxicity.

DETAILED DESCRIPTION

The fibrinolytic venom fraction is isolated by the combination of diverse fractionations, i.e., fractionation according to distinct properties and characteristics of the substance. After each fractionation, the separated fraction is assayed to determine fibrinolytic activity, as hereinafter described, and thus selected. Accordingly, purification of the venom from the Southern Copperhead snake (A.c. contortrix) and the separation of the fibrinolytic enzyme therefrom is initiated by a first fractionation step in order to separate a desired portion of the wide range of venom proteins according to molecular weight, such as by molecular sieve chromatography. In the specific examples set forth, three peaks of U.V.-280 nm absorbing material were initially eluted from a Sephadex G-100 column, the second peak being predominant and exhibiting a high level of fibrinolytic activity. Azocaseinolytic (general proteinase) activity was present in both the first and second peaks, the major amount also being in the second peak.

This elutant is then further purified by a diverse fractionation such as ion exchange chromatography. For example, the material in the second peak described above was dialyzed and applied to a CM (carboxymethyl)-cellulose cation-exchange column, and, after washing, a linear gradient was initiated. Depending on the effectiveness of the gradient, six or seven 280 nm peaks were obtained. The first peak that was eluted in the gradient contained most of the fibrinolytic activity.

In a further purification step employing a second diverse chromatographic fractionation, this peak was pooled, dialyzed and distributed on DEAE (diethylaminoethyl)-Sephadex anion-exchange chromatogram. After initiating another linear gradient, two 280 nm absorbing peaks were resolved; the first contained the majority of both the 280 nm absorbing material and the fibrinolytic and azocaseinolytic activity. Fractions of this peak were pooled and concentrated, using a membrane ultrafiltration apparatus. This material was analyzed by polyacrylamide gel electrophoresis in a protein denaturing agent (sodium dodecyl sulfate), and shown to contain a single band.

Although the enzyme prepared by the combination of molecular sieve and ion-exchange chromatographies with initial venom samples was homogeneous in that a single band was shown as described, the application of this combination to additional samples resulted in an elutant containing more than one band, thus revealing that a minor contaminating component was present. This is apparently due to the fact that different venom enzymes may be produced by different snakes and at different stages of development. In addition, sampling techniques may introduce certain enzymes which affect the desired purity. In a specific example, this impurity was determined to be a serine proteinase contaminant by the inhibition of its activity by diisopropyl fluorophosphate, a serine proteinase inhibitor. Therefore, additional purification steps involving further diverse properties are employed. For example, preparative isoelectric focusing was utilized, to remove the hemorrhagic serine proteinase contaminant. In this technique mixtures of polyaminopolycarboxylic acid ampholytes with a defined range of isoelectric points are used to establish a pH gradient across an electric field. A charged protein will migrate through a pH gradient in the electric field until it reaches a pH region in the gradient field equal to its isoelectric point. At this point the protein becomes stationary in the electric field and may be visualized and eluted from the electrofocusing gel. Proteins that differ by as little as 0.0025 in their isoelectric points can be separated on the appropriate pH gradient. Our initial demonstration of the contaminant was with broad range electrofocusing (from pH 3.5 to 9.5). By using a narrow range ampholyte solution in the pH range where the fibrinolytic enzyme focuses, an excellent preparative separation of the enzyme from the contaminant is achieved. Since the fibrinolytic enzyme focuses at about pH 6.7, ampholytes in the range from pH 5 to 7 or pH 6 to 8 are used.

Preparative isoelectric focusing has been shown to be particularly useful following molecular sieve separation and the initial ion-exchange column, to the extent that it may replace the second ion-exchange separation step herein described. Analytical isoelectric focusing and acrylamide gel electrophoresis has shown that major bands of impurities are removed by this procedure.

Affinity chromatography is an additional separation procedure which has been shown to provide substantial advantages in the terminal stages of the purification of the fibrinolytic enzyme. This method of chromatography takes advantage of an additional property of the enzyme other than molecular weight and charge, i.e., its absorption properties as to a hydrophilic compound. While this step is not as selective as other methods, it has been found to be particularly effective following the separation steps described above. In the example hereinafter set forth, dye-ligand affinity chromatography was employed to further purify samples following elution from the cation exchange column or extraction from the preparative isoelectric focusing gel. Analysis of the bound protein eluted from the dye-ligand affinity chromatography column demonstrated that major bands of impurities had been removed by this procedure.

Further, it has been found that an affinity chromatography step which binds proteolytic enzymes of the trypsin class provides substantial benefits when employed as an early step in the separation procedure, i.e., following the initial separation based upon separation according to molecular weight. Specifically, benzamidine-Sepharose or benzamidine-Agarose affinity chromatography binds and removes the trypsin class of proteolytic enzymes while other enzymes comprising primarily the desired fibrinolytic enzyme, passes through the column.

Preliminary evaluation was then performed *in vitro* against fibrin clots using the purified fibrinolytic enzyme obtained from the initial samples after molecular sieve, CM-cellulose and DEAE cellulose chromatography. Plasma was clotted with thrombin, in the presence of 0.1 mgm purified venom enzyme. The clots lysed rapidly. Because of plasmin inhibitors in this plasma system, plasmin (the physiological fibrinolytic enzyme) produced no fibrin clot lysis.

The highly purified enzyme was then evaluated *in vivo* using a rabbit embolic-fibrinolytic angiographic model. Fresh thrombi were made by adding bovine thrombin to rabbit or human blood. The clot was allowed to set and retract at room temperature for an hour. Four rabbits were anesthetized and each kidney was catheterized under fluoroscopic guidance via a femoral artery. A retracted clot was then injected into each renal artery via the arterial catheter. The purified fibrinolytic enzyme was on one side and the other kidney served as a control, being infused with isotonic saline only. Arteriograms were made at intervals of 20 to 30 minutes, and the rate of lysis on the two sides was compared. After 20–45 minutes, lysis was marked or complete on the side of infusion in each rabbit. Much less lysis had occurred on the control side.

Renal injury on the side of lysis was evaluated by gross examination and the kidney appeared normal. In the control rabbit without embolization, post-infusion arteriography showed normal parenchymal stain. Monitoring in two rabbits showed no significant electrocardiographic or manometric changes. Histologic examination was also normal in the kidney that had been infused but not embolized.

Experiments have been performed in animals in an effort to define optimal therapeutic streptokinase regimens. Models were similar to that described above, and employed autologous or human clots in dogs, pigs, and rabbits. Increasing the rate of streptokinase infusion, or intermittent infusions of plasminogen proved ineffective in significantly accelerating clot lysis. No advantage of selective versus non-selective infusion could be demonstrated. As opposed to this experience, the venom fraction has produced remarkable and consistent lysis and both autologous and heterologous thrombi have lysed promptly. A dramatic advantage of the selective infusion has been demonstrated, since the contralateral thrombus, perfused by recirculating venom only, showed much less lysis. Indeed, the amount of contralateral lysis differed in no apparent degree from the naturally occurring lysis that has been observed on multiple prior studies.

In summary, the thromboembolic model studies revealed that the fibrinolytic enzyme has produced remarkable and consistent thrombolysis. The autologous thrombus has lysed promptly. The lack of physiologic alterations attributable to the purified fibrinolytic enzyme and the absence of demonstrable histologic changes exemplify the favorable therapeutic potential of this agent.

In contrast to the effects of known thrombolytic agents such as urokinase or streptokinase, the venom enzyme acts by direct fibrinolysis. Using highly purified (plasminogen free) fibrinogen to prepare fibrin plates, the venom enzyme produced zone clearance, indicating a direct lytic effect. Furthermore, using hydrolysis of a synthetic substrate used to measure plasmin activity (S-2251, H-D-Val-Leu-Lys-p-nitroanalide) to assay plasmin generation, the enzyme did not convert purified human plasminogen to plasmin.

Further, investigations have shown that the venom fibrinolytic enzyme is a metalloproteinase, since it is inhibited by metal chelators such as EDTA and o-phenanthroline. Also, $\alpha_2$-macroglobulin, a broad acting plasma antiproteinase, inhibits azocaseinolytic activity of the fibrinolytic enzyme. It is known that $\alpha_2$-macroglobulin inhibits metalloproteinases as well as serine proteinases.

EXAMPLES

I. Purification of the Fibrinolytic Enzyme from Southern Copperhead Venom

A. Moleculer Seive Chromatography

Figure 1:
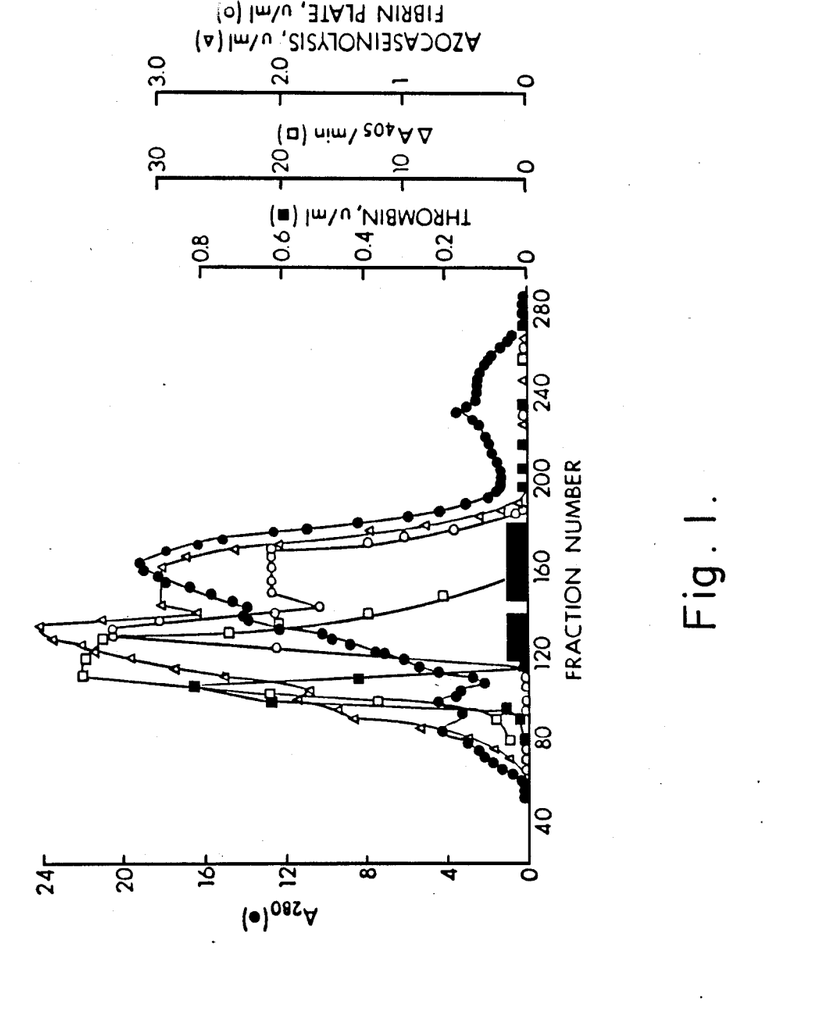
FIG. 1 shows the elution profile of crude Southern Copperhead venom from Sephadex G-100.

Venom was obtained from Biotoxins, Inc., St. Cloud, Fl., and from two to seven grams of venom were used for enzyme isolation. The procedure for a two gram preparation is now described wherein all operations were performed at 0°–4° C. The venom was dissolved in a minimal volume (2–5 ml/gram) of 0.04M Tris-HCl buffer, pH 7.1, containing 0.14M NaCl, and applied to a Sephadex G-100 column (2.5×100 cm, or 5×85 cm for larger quantities) equilibrated in the same buffer. Elution was performed at a flow rate of 10–15 ml per hour with this buffer using a Buchler monostaltic pump. Fractions of about 2 ml were collected. Column fractions were analyzed for fibrinolytic and azocaseinolytic activity as described below. Fibrinogen clotting, hydrolysis of a kallikrein chromogenic substrate, and absorbance at 280 nm were also analyzed as hereinafter described. As seen in FIG. 1, three 280 nm absorbing peaks were obtained and the latter portion of the second peak, containing the bulk of the fibrinolytic activity, was pooled as indicated by the solid boxes. The described procedure is employed to select molecular weights of from about 18 to 32 kilodaltons, and serves to eliminate proteins above and below this range.

B. Cation Exchange Chromatography

Figure 2:
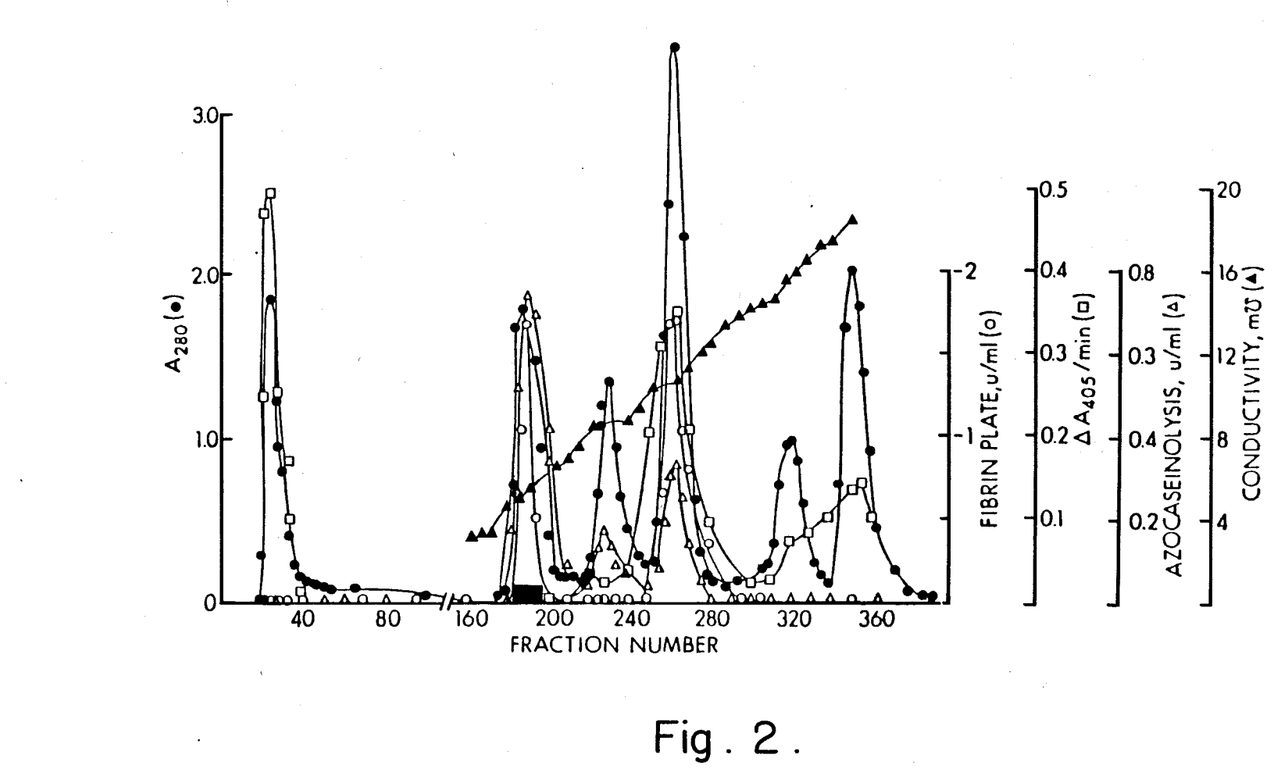
FIG. 2 shows the elution profile of the pooled fibrinolytic fractions from G-100 on CM-cellulose (CM-52)

Fractions from the Sephadex G-100 column were pooled as indicated in FIG. 1 to eliminate chromogenic substrate hydrolyzing activity, and then dialyzed against 5 mM sodium acetate, pH 6.5, and applied to a 2.5×40 cm column of CM-cellulose (CM-52). Elution was intitially performed with the 5 mM sodium acetate buffer. Fractions of about 3.5 ml were collected at a flow rate of 20–25 ml per hour. After collecting approximately 50 fractions, a linear two-step gradient was applied using initially 200 ml of the starting buffer and 200 ml of 100 mM sodium acetate buffer, pH 6.5. At fraction 145 the second gradient was initiated from 100 mM sodium acetate to 500 mM sodium acetate, pH 7.0. As seen in FIG. 2, two peaks of fibrinolytic activity were observed using the fibrin plate assay. Azocaseinolytic and S-2302 (D-Pro-Phe-Arg-p-nitroanilide) hydrolyzing activity ($\Delta A_{405}$ per minute) were also measured. Fractions containing fibrinolytic activity were pooled as indicated by the solid box. Further venom samples, purified using only steps A and B, resulted in a homogeneous fibrinolytic enzyme when assayed after elution from the CM-cellulose column.

C. Anion Exchange Chromatography

Although two fibrinolytic peaks were obtained by cation exchange (fractions 180–190 and 250–270), these peaks were pooled separately and the first fibrinolytic peak eluted was dialyzed overnight against 5 mM Tris-HCl, pH 8.3, and purified additionally on a 2.5×40 cm DEAE-cellulose (DE-52) column equilibrated in that buffer. Elution was with a linear gradient to 500 mM Tris-HCl, pH 8.3. Fractions of 4 ml were collected at a flow rate of 20–25 ml per hour.

Figure 3:
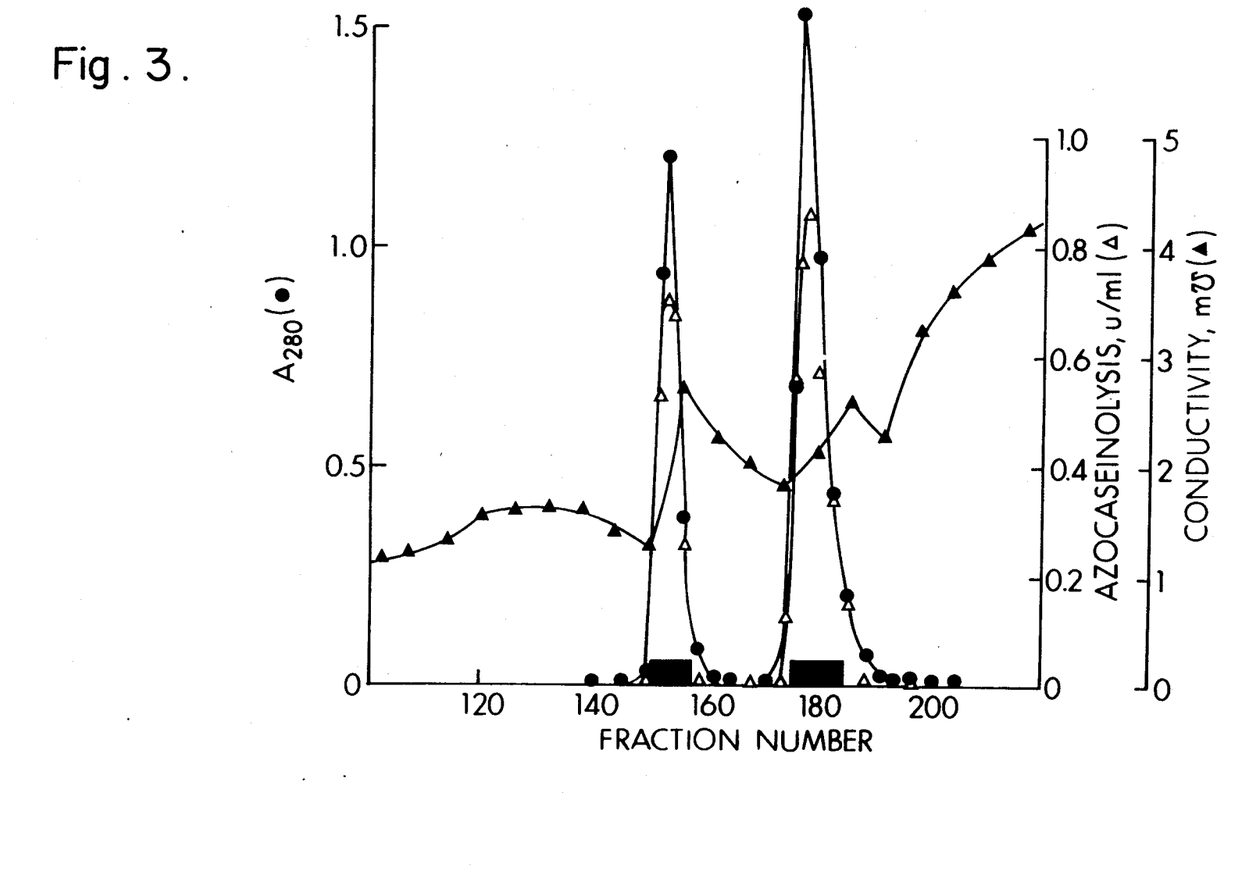
FIG. 3 shows the elution profile from DEAE-cellulose.

As seen in FIG. 3, the fibrinolytic enzyme eluted in two sharp peaks. Both peaks exhibited fibrinolytic activity on fibrin plates. Differences between the two chromatographic forms of the enzyme may be due to a gradient anomaly during chromatography, or it may be due to microheterogeneity of the enzyme caused by slightly different carbohydrate compositions.

D. Preparative Isoelectric Focusing

The venom sample obtained after CM-52 chromatography as described above was dialyzed against 1% glycine, pH 7.08, with three changes of the glycine solution. Electrofocusing was performed using a preparative system, LKB Instrument Co., Inc., Multiphor ™ horizontal flatbed, pH range 6–8. Four grams of ultrodex gel (obtained from LKB) was added to a solution of 5 ml ampholine and 95 ml H$_2$O with continuous mixing. The solution was poured onto a leveled, horizontal glass tray (125 cm×260 cm) and 36% of the water was evaporated. An additional 4 g was evaporated to allow for the sample application. The dialyzed sample (6 ml) was carefully added at the cathode end to the surface of the gel drop by drop. Power was applied and maintained at 15 watts with an EC 500 ™ power supply. Final voltage was 1800 volts for thirty minutes to sharpen the zones. Cooling was maintained at 5° C. during the entire run. A quick print of the gel was made using Whatman #1 paper and this was then stained with Coomassie G250 stain in dilute perchloric acid (57 ml per liter). The different protein zones were visualized by the blue staining bands and the corresponding regions of the gel were eluted. Each protein zone in the gel was scooped into a 6 cc syringe with a glass wool plug. Proteins were then eluted with distilled water. Readings of pH were taken on the eluted samples and recorded.

A$_{280}$, azocasein hydrolysis, fibrinolytic activity (fibrin plate) and pro-phe-arg-p-nitroanilide hydrolyzing activity was assayed on all fractions as previously described, and demonstrated the isolation of a nearly homogeneous enzyme.

E. Dye-Ligand Affinity Chromatography

A micro column was used containing 2 ml of Matrex ™ gel Red A obtained from Amicon Corporation. The gel was washed in 8M urea and allowed to sit overnight. Urea was then washed out using 20 mM Tris HCl, pH 7.5. Venom samples after CM-cellulose chromatography or isoelectric focusing were concentrated on an Amicon concentrator using a YM-10 membrane. After concentration the sample was dialyzed against the 20 mM Tris buffer.

The resulting sample (3 ml) was added to the column in 0.6 ml amounts, with a twenty minute incubation between each addition. Unbound protein was washed off with 20 mM Tris buffer. The bound protein was eluted using 20 mM Tris containing 1.5M KCl, pH 7.5, alternatively a saline gradient was used for elution. Fractions were collected and assayed by the methods described earlier for 280 nm absorbance, azocaseinolytic and fibrinolytic (fibrin plate) activity. Three or four protein peaks were obtained which demonstrated this to be an effective purification procedure.

F. Removal of Trypsin-Class Proteolytic Enzymes

Since the balance of venom composition is disturbed by each of the fractionations described above, it has become apparent that certain proteolytic enzymes naturally occurring in the venom may act on the desired fibrinolytic enzyme as the fractionation progresses. Accordingly, it is advantageous to remove the trypsin class of proteolytic enzymes by affinity chromatography, such as a benzamidine-Sepharose or benzamidine-Agarose column, as soon as possible in the separation procedure.

The pool from the Sephadex G-100 molecular sieve column was mixed with 0.10 molar borate buffer, pH 8.5 and applied to a benzamidine-Sepharose column, and washed with that buffer. Passage through this column caused the trypsin-class of proteolytic enzymes to sorb, and the fraction containing a majority of the fibrinolytic enzyme to elute in the mobile phase. Further washing with 0.10 molar borate buffer containing 0.4 molar sodium chloride caused additional portions of the fibrinolytic enzyme containing fraction to elute, although additional proteins were also released. The affinity-bound proteins were eluted by a 0.10 molar borate buffer containing 0.15 molar benzamidine, and identified as including trypsin-class proteolytic enzymes.

II. Characterization of the Fibrinolytic Enzyme

A. Molecular Weight

Figure 4:
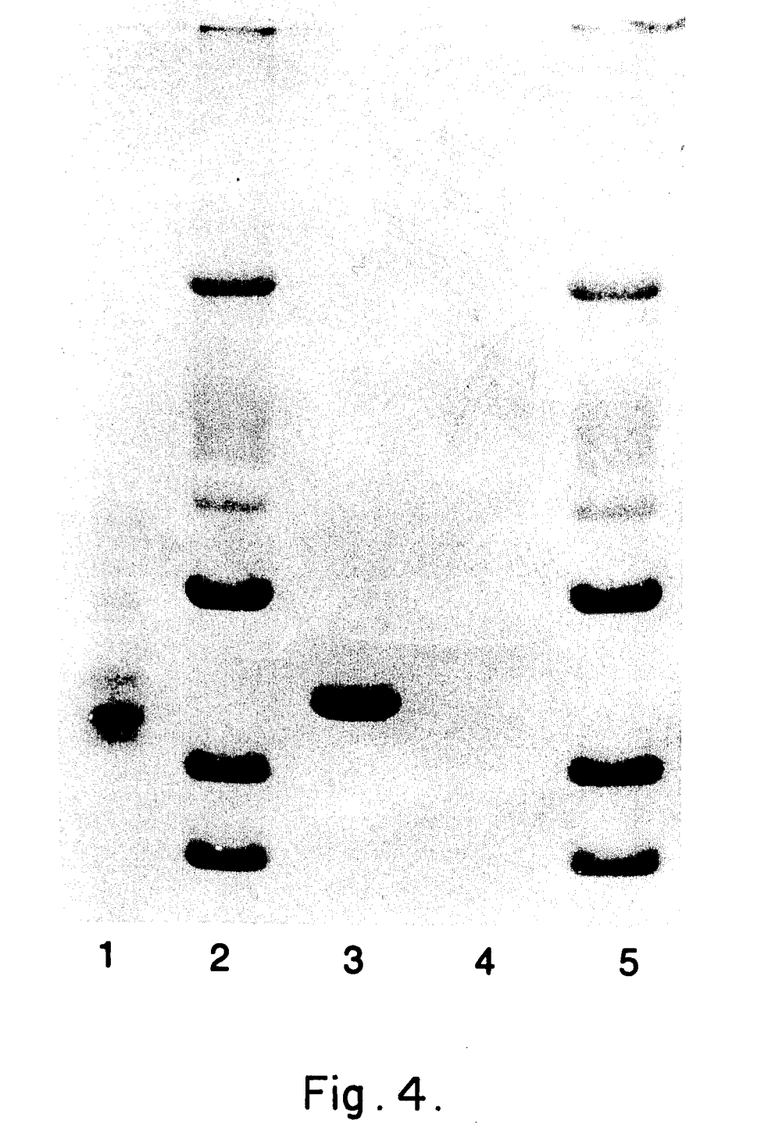
FIG. 4 shows the results of the vertical SDS-acrylamide slab gel electrophoresis (12.5% gel) of the crude venom and fibrinolytic venom fractions.

Vertical SDS-acrylamide slab gel electrophoresis (12.5% gel) was undertaken and the results are shown in FIG. 4, wherein Panel 1 is the crude venom; Panel 2, a standard protein mixture containing (from top to bottom) bovine serum albumin (Mr=66,000, ovalbumin (Mr=45,000), glyceraldehyde 3-phosphate dehydrogenase (Mr=36,000), carbonic anhydrase (Mr=29,000), trypsinogen (Mr=24,000), soybean trypsin inhibitor (Mr=20,100) and $\beta$-lactalbumin (Mr=14,200); Panel 3, purified fibrinolytic enzyme from DEAE-cellulose column; Panel 4, blank; and Panel 5, same as Panel 2. Protein staining was with Serva Violet 49. Thus, the enzyme was determined to have a single molecular weight component of between 25 and 27 kilodaltons.

B. Isoelectric Point

Figure 5:
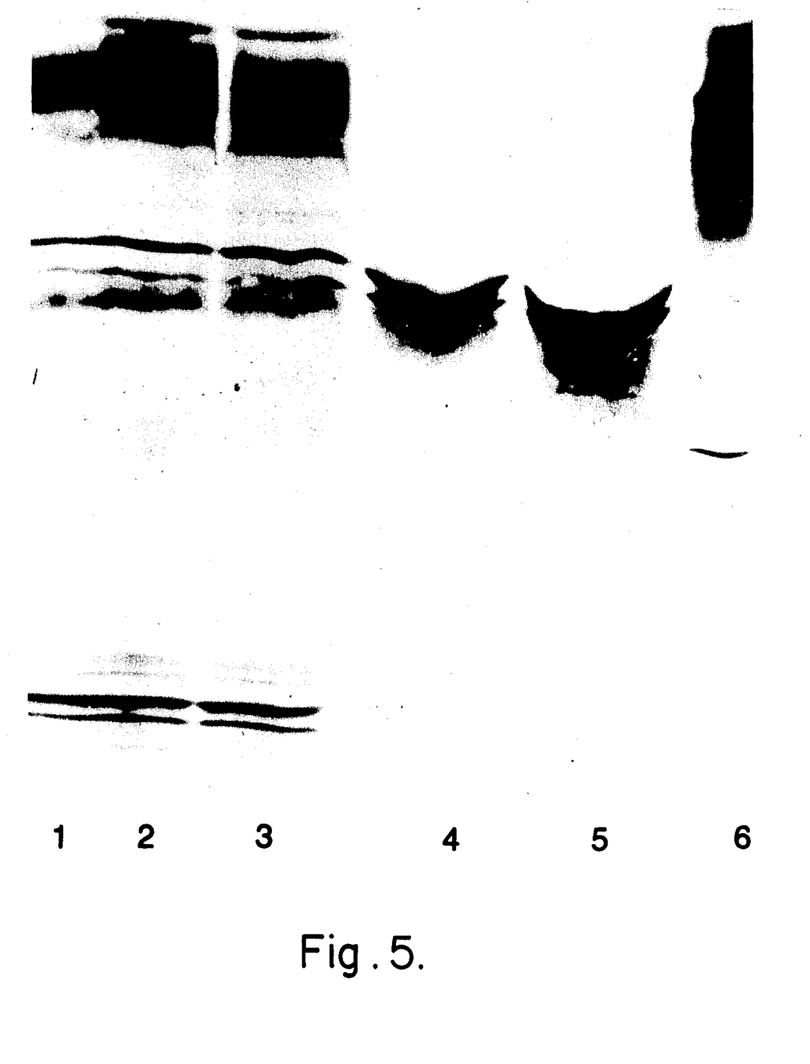
FIG. 5 shows the isoelectric focusing of the crude venom and fibrinolytic venom fractions.

Flat bed isoelectric focusing using the LKB preparative focusing apparatus and broad range Multiphor (TM, LKB Instruments, Inc.) Ampholine PAG-plate (TM, LKB Instruments, Inc.) (pH 3.5–9.5) revealed the isoelectric point of the fibrinolytic enzyme was approximately pH 6.5–7.0, as shown in FIG. 5. In that figure, panels 1, 2 and 3 are three separate lots of crude southern copperhead venom, Panel 4 is the purified fibrinolytic enzyme after DEAE-cellulose chromatography as described, Panel 5 is purified enzyme after CM-cellulose, and Panel 6 shows the hemoglobin standard for electrofocusing (pI=7.8). Protein staining was done with Serva Blue W.

C. Lack of Plasminogen Activation

In contrast to the action of streptokinase, (the agent currently in clinical use for thrombolytic therapy and which functions as a plasminogen activator), the fibrinolytic enzyme appears to act directly on fibrinogen. Using highly purified (plasminogen free) fibrinogen to prepare fibrin plates, the enzyme produced zone clearance, indicating a direct lytic effect. Furthermore, studies using hydrolysis of the plasmin substrate S-2251 (H-D-Val-Leu-Lys-p-nitroanilide) to assay plasmin generation, show that the enzyme does not convert purified human plasminogen to plasmin.

Specifically, the plasminogen activator activity of the venom enzyme was also tested as follows: purified human plasminogen (186 $\mu$g) was incubated with venom enzyme (18 $\mu$g) at 37° C. in a total volume of 0.5 ml of 0.05M TRIS-0.15M NaCl, pH 7.4. At time intervals 50 $\mu$l aliquots were taken and treated with mercaptoethanol in sodium dodecyl sulfate (SDS) containing phosphate buffer (0.1% $\beta$-mercaptoethanol-0.1% SDS-0.1M sodium phosphate, pH 7.1). The samples were analyzed by acrylamide disc gel electrophoresis according to the method of Weber and Osborn (Weber, K. and Osborn, M., *J. Biol. Chem.* 244, 4405–4412, 1969). After staining the gels with Coomassie blue the protein bands from the heavy and light chains of plasmin were not found in samples even after five hours of treating plasminogen with the venom enzyme. This example thus confirmed the lack of plasminogen activator activity in the isolated venom fraction.

D. Lack of plasminogen activation by venom enzyme as measured by S-2251 hydrolysis In addition, purified human plasminogen (62 $\mu$g) was treated with venom enzyme (3.1 $\mu$g) in 1.0 ml of 0.05M Tris-0.15M NaCl, pH 7.4 and incubated at 37° C. Aliquots from the incubation mixture were taken at various time intervals for assay of any plasmin formed in the incubation mixture. The plasmin specific substrate H-D-val-leu-lys-p-nitroanilide (S-2251)(100 $\mu$l from a 3.5 mM stock solution) was added to 900 $\mu$l 0.05M Tris-0.15M NaCl, pH 7.4 buffer, followed by the aliquot from the venom enzyme - plasminogen incubation mixture. The reaction mixture was incubated for three minutes at 37° C. and after adding 100 $\mu$l of 50% acetic acid, the absorbance of the sample at 405 nm was read in a spectrophotometer. No plasmin activity was detected in aliquots taken from the venom enzyme-plasminogen mixture incubated for as long as six hours. In separate experiments, aliquots from the incubation mixture were treated with the plasminogen activator, streptokinase. S-2251 hydrolyzing activity was generated in this experiment indicating that plasmin had been formed. These results showed that the venom enzyme not only did not activate plasminogen to plasmin but also did not degrade human plasminogen to an inactive form since it was still activatable with streptokinase.

E. Activity in the Presence of Inhibitors

Using azocasein as substrate, venom enzyme (3.5 $\mu$g) in 100–200 $\mu$l was preincubated separately at room temperature or 37° C. for 10–60 minutes with the inhibitors prior to assay, and several inhibitors of the fibrinolytic enzyme were found, as shown in Table 1. The venom enzyme thus appears to be a metalloproteinase since it is inhibited by EDTA and o-phenanthroline. A plasma antiproteinase, $\alpha_2$-macroglobulin, also inhibits azocaseinolytic activity of the fibrinolytic enzyme. It is known that $\alpha_2$-macroglobulin inhibits metalloproteinases as well as serine proteinases. The enzyme is not inhibited by diisopropylfluorophosphate or p- chloromercuribenzoate indicating that it is not a serine or cystine proteinase.

TABLE 1

| Inhibition of Azocaseinolytic Activity | |
| --- | --- |
| Inhibition | No Inhibition |
| EDTA ($5 \times 10^{-2}$ M) 92% inhibition | Trasylol (100 KIU) |
| $\alpha_2$-Macroglobulin 95% inhibition (300 µg) | Lima bean trypsin inhibitor (100 µg) |
| | Soybean trypsin inhibitor (100 µg) |
| | Diisopropylfluorophosphate (100 mM) |
| | p-Chloromercuribenzoate (1 mM) |

III. In Vitro Activity

A. Fibrin Plate Assay

Fibrinolytic activity was measured by fibrin plate assay, performed as follows. 1.02 g of Kabi human fibrinogen (containing salts plus protein) was dissolved in 6 ml of fibrin plate buffer. This buffer is made by dissolving 20.62 g sodium barbital in 1350 ml H$_2$O and adding 500 ml of 0.1N HCl and 100 ml of salt solution, as described, adjusting the pH to 7.75 with 0.1N HCl and adding water to 2000 ml. The salt solution is composed of 4.89 g CaCl$_2$ - 2H$_2$O, 2.79 g MgCl$_2$-6H$_2$O, 109.12 g NaCl dissolved in distilled water and diluted to 100 ml. This solution improves clot structure and makes the lysed zone clearly demarcated. The fibrinogen solution was then dialyzed against 4 l of 0.9% NaCl for one day at 4° C. and one day at room temperature. The absorbance of the fibrinogen solution at 280 nm was determined and the fibrinogen diluted to 1.6% (16 mg/ml) using the fibrin plate buffer. 6.2 ml of the 1.6% fibrinogen was then added to 40 ml of the fibrin plate buffer and water added to adjust the final the final volume to 50 ml. The fibrin plate was poured using 100×15 mm disposable polystyrene Petri dishes. Six ml of the fibrinogen solution was pipetted into the plate and then 0.2 ml of Parke-Davis topical bovine thrombin was added with rapid stirring. The thrombin was diluted to 8 units per 0.2 ml in saline-barbital buffer with gelatin, made by dissolving 5.85 g NaCl and 10.31 g sodium barbital in 725 ml distilled water and adding 200 ml 0.1N HCl containing 2.5 g of gelatin (laboratory grade, granular). Distilled water was then added to adjust the final volume to 1 l, pH 7.75. Six wells of 2 mm diameter were formed in the fibrin plate after sitting two hours at room temperature to allow the fibrin gel to form. 10 µl of the venom fractions or standard plasmin were added to the plate and it was incubated overnight (17 hours) at 37° C. Lysis was analyzed by measuring (in mm) the clear zones produced around the wells. Activity is expressed in plasmin equivalent units/ml (a plasmin preparation (10.5 caseinolytic units/ml) was used as a standard).

Figure 6:
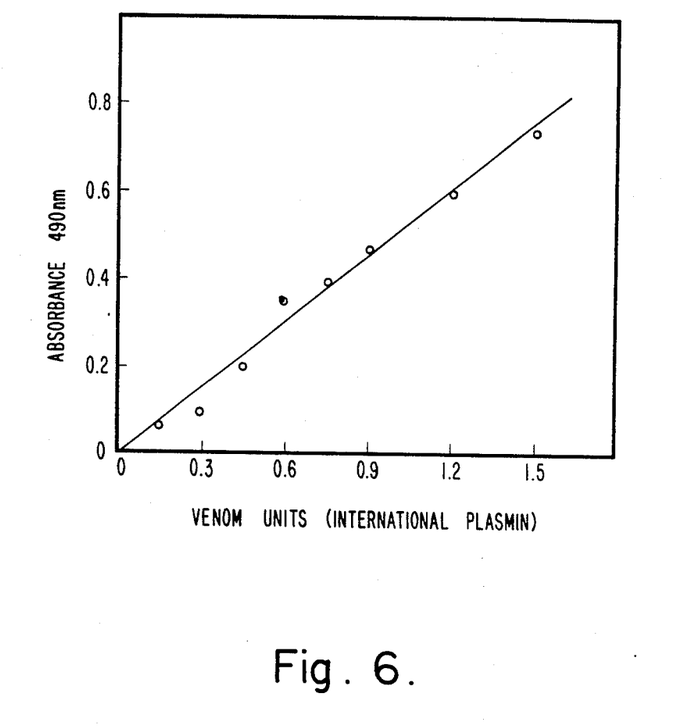
FIG. 6 shows the standardization of the fibrinolytic venom enzyme against international standard plasmin.

Azocaseinolytic activity was assayed by adding column fractions directly to azocasein and measuring the hydrolysis products at 390 nm. Fractions of 10 µl were added to 1.0 ml of 1.5% azocasein (made in 0.1M sodium borate, pH 8.5) and incubated at 37° C. for 60 minutes. To stop the reaction, 1.0 ml of perchloric acid (1.16M) was added and the mixture was allowed to sit at room temperature for 10 minutes. The reaction mixture was centrifugated for 10 minutes and the supernatant was removed, recentrifuged as above and the absorbance at 390 nm was measured. The results are shown in FIG. 6, wherein activity is expressed in equivalent plasmin azocaseinolytic units/ml (assayed against a plasmin standard), and 0.716 µg of venom enzyme is seen to equal 0.15 units standard plasmin (1 mg of venom enzyme=210 plasmin units). This can be compared to plasmin activity, which is 30–35 units per mg of pure plasmin.

B. Fibrinogen Clotting Assay

To help localize the thrombin-like enzyme in this venom, aliquots of column fractions were assayed for fibrinogen clotting activity at 37° C. by measuring the time for clot formation after adding 100 µl of an appropriate dilution of the fraction to a prewarmed (3 minutes, 37° C.) test tube containing 200 µl of a 1% human fibrinogen solution (Kabi) dialyzed against 0.04 Tris-HCl, 0.14 sodium chloride, pH 7.35. Standard thrombin was used to generate a clotting curve. Activity is expressed in N.I.H. equivalent thrombin clotting units per milliliter.

C. Kallikrein Chromogenic Substrate Assay

Hydrolysis of the kallikrein chromogenic substrate Pro-Phe-Arg-p-nitroanilide in 0.05M Tris-HCl buffer, pH 7.5, containing 0.15M NaCl, was also employed to localize proteolytic enzymes that may contaminate the fibrinolytic enzyme (which is devoid of chromogenic substrate hydrolyzing activity). For these assays, 10 to 100 µl of column fraction was brought to 900 µl with the Tris buffer and incubated for 3 minutes at 37° C. Then 100 µl of the chromogenic substrate in 20% methanol was added to give a final substrate concentration of 0.6 mM. The reaction was allowed to proceed for 3 minutes at 37° C. and 100 µl of 50% acetic acid was added to stop the reaction. The absorbance at 405 nm was then determined and plotted as $\Delta A_{405}$ per minute.

D. Plasma Clot Lysis

Human and rabbit plasma (anticoagulated with 1/10 volume of 3.8% sodium citrate) were used to measure in vitro fibrin clot lysis. Plasma (0.5 ml) was clotted by the addition of an equal volume of thrombin (12.5 NIH units, Parke Davis, topical) in the presence of 0.18 mg of the purified venom enzyme (assuming 1.0 $A_{280}$ units is equivalent to 1 mg/ml) or plasmin. Clot lysis time for the venom enzyme with the human clot was 137 minutes and for the rabbit clot 134 minutes. By comparison plasmin (1.08 caseinolytic units per milliliter) did not lyse the human or rabbit plasma clots even after twenty-four hours.

IV. In Vivo Studies

Figure 7:
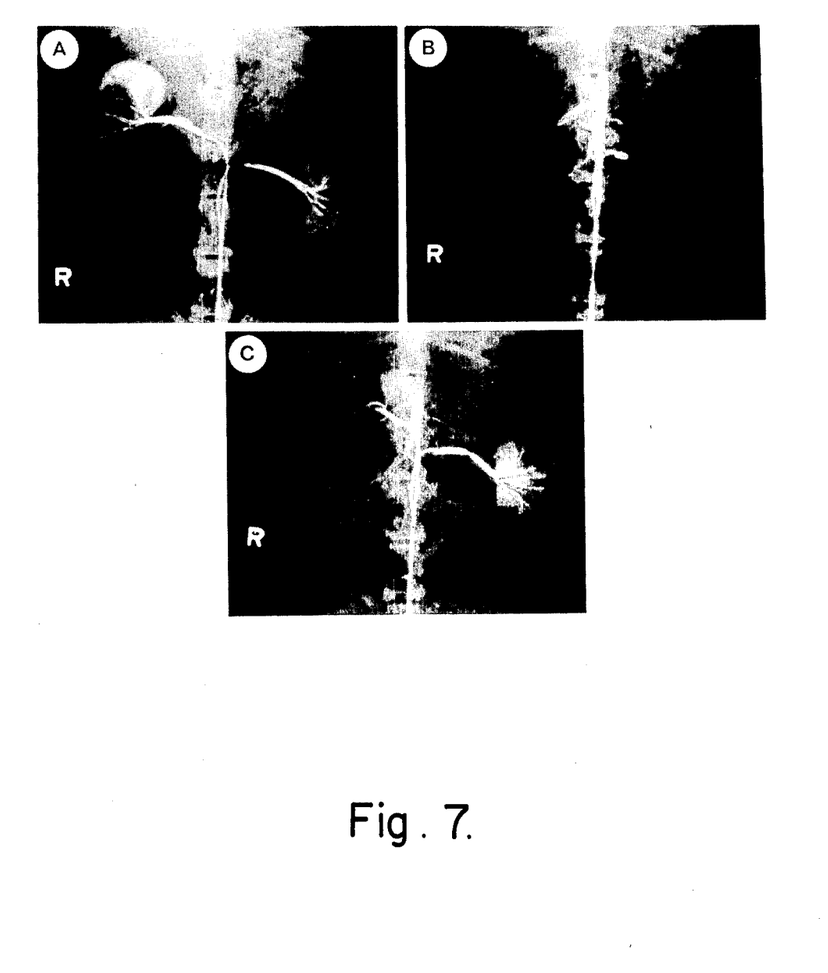
FIG. 7 shows arteriograms of a rabbit embolic-fibrinolytic angiographic model.

The fibrinolytic enzyme, purified as herein described, was tested in vivo, using a rabbit embolic-fibrinolytic angiographic model. Toxicity was tested by infusing venom into normal rabbit kidneys. The rabbit was selected as the experimental animal for convenience and economy. Fresh thrombi were made by adding bovine thrombin to rabbit blood. Clots were allowed to set and retract at room temperature for one hour. Four rabbits were anesthetized and each kidney was catheterized under fluoroscopic guidance via a femoral artery. Control arteriograms were performed by simultaneously injecting each kidney with contrast medium, followed by serial films. A magnification technique (2.5×) was employed. A retracted clot, approximately 0.25 ml, was then injected into each renal artery via the arterial catheters. The existence of complete arterial occlusion was confirmed fluoroscopically and additional clot was injected, if necessary, until the artery was completely obstructed. The animal was then heparinized (1 mg heparin/kg by intravenous infusion, followed by 0.1 mg/kg per hour thereafter). Five minutes later, a repeat arteriogram was obtained for documentation. Within 10 minutes after the post-embolic arteriogram, infusion of the fibrinolytic enzyme was begun on one side; the other kidney served as a control and was infused with isotonic saline only. On the test side, the enzyme was infused at the rate of 0.1 ml per minute, using a concentration of 1 mg/ml of purified enzyme in physiological saline solution, for a period of thirty-sixty minutes. Arteriograms were repeated at intervals of twenty to thirty minutes, and the rate of lysis on the two sides was compared. Typical results are shown in FIG. 7, wherein the arteriograms show: (A), contrast medium injected through catheters into both normal renal arteries; (B), arterial occlusion after introducing thrombus in both renal arteries; (C), after infusion of the purified fibrinolytic enzyme into the occluded left renal artery, almost complete clearance of the clot at thirty minutes. Note the lack of clearance in the non-infused (right) kidney. After four hours, the right renal artery remained occluded, but then cleared after a twenty minute selective infusion of the venom enzyme into the right renal artery (not shown). In summary, lysis was marked or complete on the side of infusion in each rabbit after thirty minutes. Much less lysis had occurred on the control side.

Toxicity was tested in two additional rabbits. The left carotid artery in each rabbit was operatively exposed, and cannulated with a needle, through which arterial pressures were recorded. Needle electrodes were placed on three limbs, enabling continuous EKG recording. Monitoring in these rabbits showed no significant electrocardiographic or manometric changes following infusion of the venom enzyme into normal rabbit kidneys.

In one additional rabbit, venom was infused into one kidney for 35 minutes, in the absence of thrombus, to evaluate possible tissue injury secondary to the venom enzyme. Bilateral arteriograms were performed before and after infusion and two days thereafter. Blood levels of urea nitrogen and creatinine were determined and kidneys were examined histologically after two days. No arteriographic, histologic, or functional evidence of injury was apparent.

In summary, as individual samples of venom may comprise various distributions of different protein fractions, it should be noted that the diverse separation steps herein described are employed to the extent required to produce a homogeneous enzyme moiety producing the desired fibrinolytic activity. For example, the homogeneous fractions used in the *in vitro* and *in vivo* studies herein set forth were obtained by the initial separation of proteins of from about 20 to 32 kd, followed by separation of the 20 to 32 kd fraction by means of ion exchange chromatography. With regard to another sample, a homogeneous enzyme was obtained by molecular size and cation exchange separation only. However, due to such sample variations, the overall reliability of the separation process is substantially improved by the inclusion of additional separation techniques based on diverse physical properties of the enzyme and other venom fractions, such as the removal of proteolytic contaminants and the use of isoelectric focusing and various forms of affinity chromatography as described.

The enzyme is applied thereapeutically as described herein in concentrations of from about 0.1 to 1.0 mg/ml in physiological saline solution, although other appropriate carriers and techniques which are known in the art may be employed depending upon the particular treatment required. In addition, dosages are similarly adjusted, although elevated dosages create an increased risk of possibly adverse systemic response.

While the invention has been described in some detail by way of illustration and example, changes in form and the substitution of equivalents and equivalent venoms are contemplated as circumstances may suggest or render expedient. Although specific terms have been employed herein, they are intended in a descriptive sense and not for purposes of limitation, the scope of the invention being delineated in the following claims.

What is claimed is:

1. A process for the separation of an enzyme from snake venom comprising:

separating the venom of the Southern Copperhead snake, A.c. contortrix, into molecular weight fractions and selecting the fraction containing proteins having molecular weights of from about 20 to 32 kd; and extracting a metalloproteinase having a molecular weight of from about 25 to 27 kd, an isoelectric point of 6.5 to 7.0 and exhibiting a direct fibrinolytic activity in the essential absence of plasmin activation from the 20 to 32 kd fraction by a method or methods selected from the group consisting of ion-exchange chromatography, preparative isoelectric focusing and affinity chromatography.

2. The process of claim 1 wherein the 20 to 32 kd fraction is purified by members of the group consisting of
   a. affinity chromatography which binds the trypsin class of proteolytic enzymes,
   b. cation exchange chromatography,
   c. anion exchange chromatography,
   d. preparative isoelectric focusing, and
   e. dye ligand chromatography.

3. A method for the treatment of thromboembolic disease in a patient, comprising administering to such patient a metalloproteinase isolated from the Southern Copperhead snake, A.c. contortrix and having a molecular weight of from about 25-27 kd and an isoelectric point of 6.5 to 7.0, and characterized by the exhibition of a direct fibrinolytic activity in the essential absence of plasmin activation, said metalloproteinase being administered in the presence of a pharmaceutically acceptable carrier therefor.

* * * * *